(12) United States Patent
Rieth et al.

(10) Patent No.: US 8,828,917 B2
(45) Date of Patent: *Sep. 9, 2014

(54) CARBOXY ESTER KETAL REMOVAL COMPOSITIONS, METHODS OF MANUFACTURE, AND USES THEREOF

(75) Inventors: Lee R. Rieth, Plymouth, MN (US); Matthew J. Tjosaas, Minneapolis, MN (US); Dorie J. Yontz, Bloomington, MN (US)

(73) Assignee: Segetis, Inc., Golden Valley, MN (US)

( * ) Notice: Subject to any disclaimer, the term of this patent is extended or adjusted under 35 U.S.C. 154(b) by 165 days.

This patent is subject to a terminal disclaimer.

(21) Appl. No.: 13/208,797

(22) Filed: Aug. 12, 2011

(65) Prior Publication Data

US 2012/0040880 A1 Feb. 16, 2012

Related U.S. Application Data

(60) Provisional application No. 61/394,374, filed on Oct. 19, 2010, provisional application No. 61/372,972, filed on Aug. 12, 2010.

(51) Int. Cl.
| | | |
|---|---|---|
| C11D 3/60 | (2006.01) | |
| A61K 8/39 | (2006.01) | |
| C11D 3/20 | (2006.01) | |
| A61Q 19/10 | (2006.01) | |
| A61K 8/49 | (2006.01) | |
| C11D 7/26 | (2006.01) | |
| C23G 5/032 | (2006.01) | |
| A61K 8/92 | (2006.01) | |

(52) U.S. Cl.
CPC ............... *C11D 3/2093* (2013.01); *A61K 8/39* (2013.01); *C11D 3/2096* (2013.01); *A61Q 19/10* (2013.01); *A61K 8/4973* (2013.01); *C11D 7/266* (2013.01); *C23G 5/032* (2013.01); *A61K 8/92* (2013.01); *C11D 7/267* (2013.01)
USPC ............ 510/138; 510/392; 510/395; 510/401

(58) Field of Classification Search
USPC .................................. 510/138, 392, 395, 401
See application file for complete search history.

(56) References Cited

U.S. PATENT DOCUMENTS

| | | | |
|---|---|---|---|
| 1,934,309 A | 11/1933 | Hoover | |
| 2,008,720 A | 7/1935 | Lawson | |
| 2,260,261 A | 10/1941 | Morey et al. | |
| 2,556,135 A | 6/1951 | Croxall et al. | |
| 2,654,723 A | 10/1953 | Greene | |
| 2,985,536 A | 5/1961 | Stein et al. | |
| 3,201,420 A | 8/1965 | Fuzesi et al. | |
| 3,658,789 A | 4/1972 | Fried | |
| 3,855,248 A | 12/1974 | Lannert et al. | |
| 4,460,767 A | 7/1984 | Matsumura et al. | |
| 4,737,426 A | 4/1988 | Roth | |
| 4,792,411 A | 12/1988 | Walsh | |
| 4,806,448 A | 2/1989 | Roth | |
| 5,013,543 A | 5/1991 | Mercado et al. | |
| 5,093,111 A | 3/1992 | Baker et al. | |
| 5,419,848 A | 5/1995 | Van Eenam | |
| 5,516,459 A | 5/1996 | Van Eenam | |
| 5,700,522 A | 12/1997 | Nonweiler et al. | |
| 5,705,087 A | 1/1998 | Mushrush et al. | |
| 5,886,136 A * | 3/1999 | Tanaka et al. ................ | 528/353 |
| 5,998,092 A | 12/1999 | McCulloch et al. | |
| 6,010,995 A | 1/2000 | Van Eenam | |
| 6,034,118 A | 3/2000 | Bischofberger et al. | |
| 6,130,195 A | 10/2000 | Doyel et al. | |
| 6,239,087 B1 * | 5/2001 | Mao et al. ..................... | 510/101 |
| 6,306,249 B1 | 10/2001 | Galante et al. | |
| 6,372,791 B1 | 4/2002 | Shapiro et al. | |

(Continued)

FOREIGN PATENT DOCUMENTS

| | | |
|---|---|---|
| CA | 1000285 | 11/1976 |
| CA | 2347255 A1 | 2/2004 |

(Continued)

OTHER PUBLICATIONS

Boehm, R., "Knowledge on cyclic ketals. Part 11: Synthesis of some new derivatives and separation of their isomers," Pharmazie 36(5): 329-330 (1981).

(Continued)

*Primary Examiner* — Nicole M Buie-Hatcher
*Assistant Examiner* — M. Reza Asdjodi
(74) *Attorney, Agent, or Firm* — Cantor Colburn LLP

(57) ABSTRACT

A removal composition is described, having a plurality of abrasive particles, an organic amine, antioxidant, biocide, colorant, corrosion inhibitor, cosolvent, defoamer, dye, enzyme, light stabilizer, odor masking agent, plasticizer, preservative, rust inhibitor, surfactant, thickener, or a combination comprising at least one of the foregoing; from 0 to 1% water, based on the total weight of the removal composition; and a ketal adduct of formula (1)

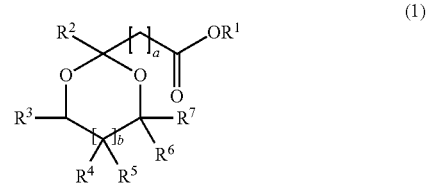

(1)

wherein $R^1$ is C1-6 alkyl, $R^2$ is hydrogen or C1-3 alkyl, each $R^3$, $R^4$, and $R^5$ is independently hydrogen or C1-6 alkyl, $R^6$ and $R^7$ are each independently hydrogen or C1-6 alkyl, a=0-3, and b=0-1.

29 Claims, No Drawings

(56) References Cited

U.S. PATENT DOCUMENTS

| | | | |
|---|---|---|---|
| 6,423,480 B2 | 7/2002 | Ichiki | |
| 6,423,677 B1 | 7/2002 | Van Eenam | |
| 6,451,223 B1 | 9/2002 | Jeon | |
| 6,528,025 B1 | 3/2003 | Boesch et al. | |
| 6,627,181 B1 | 9/2003 | Busch, Jr. et al. | |
| 6,749,998 B2 | 6/2004 | Schwartzkopf et al. | |
| 6,806,392 B2 | 10/2004 | Boesch et al. | |
| 7,094,395 B1 | 8/2006 | Qu et al. | |
| 7,179,775 B2 | 2/2007 | Foster | |
| 2002/0183234 A1 | 12/2002 | Jalalian et al. | |
| 2003/0133895 A1 | 7/2003 | China et al. | |
| 2003/0167681 A1 | 9/2003 | Delgado Puche | |
| 2004/0024260 A1 | 2/2004 | Winkler et al. | |
| 2004/0120918 A1 | 6/2004 | Lintner et al. | |
| 2004/0138090 A1 | 7/2004 | Drapier et al. | |
| 2004/0157759 A1 | 8/2004 | Scherubel | |
| 2004/0167245 A1 | 8/2004 | Chappelow et al. | |
| 2005/0233927 A1 | 10/2005 | Scherubel | |
| 2006/0069230 A1 | 3/2006 | Papisov | |
| 2006/0134045 A1 | 6/2006 | Cao et al. | |
| 2006/0207037 A1 | 9/2006 | Fadel et al. | |
| 2006/0208226 A1* | 9/2006 | Maze et al. | 252/387 |
| 2006/0211855 A1 | 9/2006 | Doring et al. | |
| 2007/0079722 A1* | 4/2007 | Parish | 102/513 |
| 2007/0111917 A1 | 5/2007 | Lang et al. | |
| 2007/0161530 A1* | 7/2007 | Kaneda et al. | 510/176 |
| 2008/0081779 A1* | 4/2008 | Holscher | 512/22 |
| 2008/0096785 A1 | 4/2008 | Egbe et al. | |
| 2008/0124426 A1* | 5/2008 | Kobler et al. | 426/2 |
| 2008/0188603 A1 | 8/2008 | Porzio et al. | |
| 2008/0242721 A1* | 10/2008 | Selifonov | 514/467 |
| 2008/0305978 A1 | 12/2008 | Wietfeldt et al. | |
| 2009/0124531 A1 | 5/2009 | Danziger et al. | |
| 2009/0281012 A1 | 11/2009 | Trivedi et al. | |
| 2010/0087357 A1 | 4/2010 | Morgan, III et al. | |
| 2010/0215775 A1* | 8/2010 | Schmaus et al. | 424/685 |
| 2011/0130470 A1* | 6/2011 | Kraft | 514/739 |
| 2011/0196081 A1 | 8/2011 | Kwon et al. | |
| 2011/0300083 A1 | 12/2011 | Yontz et al. | |
| 2012/0128614 A1 | 5/2012 | Rieth et al. | |
| 2013/0053564 A1* | 2/2013 | Selifonov et al. | 544/374 |

FOREIGN PATENT DOCUMENTS

| | | |
|---|---|---|
| DE | 3220035 A1 | 1/1983 |
| DE | 10036423 A1 | 3/2001 |
| EP | 012543 A1 | 6/1980 |
| EP | 0308956 A2 | 3/1989 |
| EP | 0507190 A1 | 10/1992 |
| EP | 0913463 A1 | 5/1999 |
| FR | 1445013 | 7/1966 |
| JP | 28004327 A | 9/1953 |
| JP | 4217972 | 8/1992 |
| JP | 07228887 A | 8/1995 |
| JP | 2005143466 A | 6/2005 |
| JP | 2006143702 A | 6/2006 |
| SU | 722912 | 3/1980 |
| WO | 9412489 A1 | 6/1994 |
| WO | 9856889 | 12/1998 |
| WO | 2004099173 A1 | 11/2004 |
| WO | 2005095378 A2 | 10/2005 |
| WO | 2005097723 A2 | 10/2005 |
| WO | 2005097724 A1 | 10/2005 |
| WO | WO2007062158 A2 | 5/2007 |
| WO | WO2008/046795 A1 | 4/2008 |
| WO | 2008089463 A2 | 7/2008 |
| WO | 2008098375 A1 | 8/2008 |
| WO | WO2009032905 A1 | 3/2009 |

OTHER PUBLICATIONS

Brigl, et al., "The Reaction of the Pyruvic Acid with Glycerin," Annalen der Chemie 476: 215-232.
Briol, et al., "Reaction of pyroracemic acid with glycerol," Ann. 476: 215-232 (1929).
Calinaud, et al., "Cyclic acetal series. XIII. Opening of 4-oxo and 4-hydroxy-3,6,8-trioxabicyclo[3.2.1]octane and 3-pxp-2,5,7-trioxabicyclo[2.2.2]octane rings by lithium aluminum hydride and methylmagnesium iodide," Carbohydrate Research 30(1) 35-43 (1973).
Carey, et al., "Advanced Organic Chemistry, Second Edition, Part B: Reactions and Synthesis," Plenum Press 539-552 (1983).
Cuiling, et al., "Synthesis of Levulinic Ketals with Furfuryl Alcohol as Raw Material," Journal of Huagiao University (Nature Science) 23(3): 257-259 (2002) (English Translation).
Gelas, et al., "Synthese du 4-oxo et de 4-hydroxy-3,6,8-trioxabicyclo[3.2.1]octanes," Carbohydrate Research 30(1): 21-34 (1973) (with English abstract).
Grosu, et al., "Stereochemistry and NMR Spectra of Some New Unsymmetrical Substituted 2,2-Dialkyl-1,3-Dioxanes," Revue Roumaine de Chimie 41(3-4): 259-263 (1996).
Gutsche, et al., "Reactions of Ethyl Diazoacetate with Aromatic Compounds Containing Hetero Atoms Attached to the Benzyl Carbon," J. Am. Chem. Soc. 76: 2236-2240 (1954).
Haskelbhrg, L., "The preparation of glycerol esters of amino acids," Compt. rend. 190270-190272 (1930).
Hegde, et al., "The Kinetics and Thermodynamics of Bicyclic Ketal Formation: An Application to the Synthesis of the Zaragozic Acids," Tetrahedron 53(32): 11179-11190 (1997).
Horsfall, et al., "Fungitoxicity of Dioxanes, Dioxolanes, and Methylenedioxybenzenes," The Connecticut Agricultrual Experiment Station New Haven, Bulletin 673: 1-44, Jun. 1965.
Lukes, Robert M., Preparation of Methyl Esters Containing the 1,3-Dioxane or 2,4,8,10-Tetroxaspiro[5.5]undecane Structure by Ketal Exchange, 26: 2515-2518 (1961).
Meltzer, et al., "2,2-Disubstituted 1,3-Dioxolanes and 2,2-Disubstituted 1,3-Dioxanes," JOC 25: 712-715 (1960).
Meskens, Frans A.J., "Methods for the Preparation of Acetals from Alcohols or Oxiranes and Carbonyl Compounds," Synthesis 501-522 (1981).
Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).
Newman, et al.,"Kinetic and Equilibrium Studies of Cyclic Ketal Formation and Hydrolysis," The Journal of the American Oil Chemist's Society 80: 6350-6355 (1958).
Olson, Edwin S., "Subtask 4.1—Conversion of Lignocellulosic Material to Chemicals and Fuels," Final Report for U.S. Dept. of Energy, National Energy Technology Laboratory, Cooperative Agreement No. DE-FC26-98FT40320 (Jun. 2001).
Ono, et al., "Synthesis and Properties of Soap Types of Cleavable Surfactants Bearing a 1,3-Dioxolane Ring Derived from Long-chain Epoxides and Ethyl Levulinate," J. Jpn. Oil Chem. Soc. 42(12): 965-971 (1993).
Wedmid, et al., "Long-Chain Stereomeric 2-Alkyl-4-methoxycarbonyl-1,3-dioxolanes in Glycerol Acetal Synthesis," J. Org. Chem. 42(22): 3624-3626 (1977).
Yamaguchi, Masahiko, "Synthesis of Polycyclic Aromatic Compounds via Polyketides," Yuki Gosei Kagaku Kyokaishi 45(10) 969-982 (1987) (Chinese—Translation of Abstract Only).
Yang, et al., "Investigation of homopolymerization rate of perfluoro-4,5-substituted-2-methylene-1,3-dioxolane derivatives and properties of the polymers," Journal of Flourine Science 127: 277-281 (2006).
Zhang, et al., "Synthesis of Ketals of 4-Oxopentanoates," Lanzhou Daxue Xuebao, Ziran Kexueban 30(2): 66-70 (1994).
Transmittal with International Preliminary Report on Patentability for PCT/US2011/047618 mailed Feb. 21, 2013, and Written Opinion of the International Searching Authority mailed Mar. 20, 2012, 8 pages.
Transmittal and International Search Report for PCT/US/2011/047618, mailed Mar. 10, 2012, 5 pages.
Transmittal and International Search Report for PCT/US2011/047620, mailed Mar. 22, 2012, 7 pages.

(56) References Cited

OTHER PUBLICATIONS

Written Opinion of the International Searching Authority for PCT/US2011/047620, mailed Mar. 22, 2012, 5 pages.
Written Opinion of the International Search Authority for PCT/US2011/047618, mailed Mar. 20, 2012, 6 pages.
Brigl, Percy, et al., "The Reaction of the Pyruvic Acid with Glycerin," Annalen der Chemie 476: 215-232 with English translation.
Holmberg, Krister, "Surfactants with controlled half-lives", Current Opinion in Colloid & Interface Science, vol. 1, Issue 5, pp. 572-579 (Oct. 1996).
Doolittle, Arthur K., "Application of a Mechanistic Theory of Solvent Action to Plasticizers and Platicization", Journal of Polymer Science, vol. 2, No. 2 (1947) 121-141.
STIC Search Report dated Jul. 5, 2013, 90 pages.

* cited by examiner

CARBOXY ESTER KETAL REMOVAL COMPOSITIONS, METHODS OF MANUFACTURE, AND USES THEREOF

CROSS-REFERENCE TO RELATED APPLICATION

This application claims the benefit of U.S. Provisional Patent Application Nos. 61/372,978 filed on Aug. 12, 2010 and 61/394,374 filed on Oct. 19, 2010, the contents of both applications being incorporated by reference herein in their entirety.

BACKGROUND

This disclosure relates to carboxy ester ketal stripping and removal compositions, methods for the manufacture of the compositions, and uses of the compositions.

In stripping and removal compositions (for example, paint stripping or graffiti or adhesive removal), solvent selection is guided by considerations such as solubility, solubilization activity, reactivity, volatility, toxicity, environmental profile, and cost. It has been theorized that the removal of undesirable paints, inks, adhesives, and the like from a substrate is accomplished by two mechanisms, namely, dissolution and/or lifting. Dissolution is when the undesirable material is dissolved from the substrate by a solvent. Lifting is when the solvent penetrates into the undesirable material and causes it to swell. As a result of the swelling, the material (whether it be a paint, coating or the like) wrinkles and lifts (separates) from the substrate, allowing the material to then be easily removed from the substrate's surface.

SUMMARY

While a number of solvents for stripping and removal compositions are available and in commercial use, there remains a need in the art for new solvents that offer a favorable combination of solubility, solubilization activity, reactivity, volatility, toxicity, environmental profile, and cost.

Further, there is an increasing need for "bio-sourced" solvents that can be used as replacements for petroleum-sourced solvents. Few bio-sourced solvents are available that can meet the increasingly demanding technical requirements for stripping and removal compositions. Even where such solvents are available, the solvents can have various drawbacks. For example, d-limonene, which has been utilized as a replacement for chlorinated solvents in degreasing applications, has a strong odor, is combustible, and is classified as an irritant and sensitizer. Similarly, ethanol is a versatile solvent that is readily available from bio-based sources, but its high flammability limits its use in solvent applications. A further drawback of these solvents is that the chemical and physical properties of the solvents can only be adjusted to a limited extent.

There accordingly remains a need in the art for alternative solvents for stripping and removal compositions, in particular bio-sourced solvents that offer an advantageous combination of solubilization activity with one or more of reactivity, volatility, toxicity, environmental profile, and cost. It would be further advantage if such solvents could be readily modified to adjust the chemical and physical properties of the solvent to meet the needs of a specific application. It would be advantageous if the bio-sourced solvents provided stripping and removal compositions that meet one or more customer needs such as good viscosity, low odor, high solubilization and/or lifting activity, and low toxicity.

A removal composition comprises a plurality of abrasive particles, an organic amine, antioxidant, biocide, colorant, corrosion inhibitor, cosolvent, defoamer, dye, enzyme, light stabilizer, odor masking agent, plasticizer, preservative, rust inhibitor, surfactant, thickener, or a combination comprising at least one of the foregoing; from 0 to 1% water, based on the total weight of the removal composition; and a ketal adduct of formula (1):

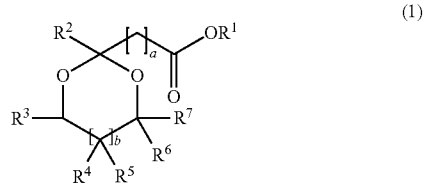

wherein
$R^1$ is C1-6 alkyl,
$R^2$ is hydrogen or C1-3 alkyl,
each $R^3$, $R^4$, and $R^5$ is independently hydrogen or C1-6 alkyl,
$R^6$ and $R^7$ are each independently hydrogen or C1-6 alkyl,
a=0-3, and
b=0-1.

A method of preparing the removal composition comprises combining a plurality of abrasive particles, an organic amine, antioxidant, biocide, colorant, corrosion inhibitor, cosolvent, defoamer, dye, enzyme, light stabilizer, odor masking agent, plasticizer, preservative, rust inhibitor, thickener, or a combination comprising at least one of the foregoing and the above-described ketal adduct of formula (1).

A method of removing material on a surface of a substrate comprises contacting the material on the surface of the substrate with the above-described removal composition under removal conditions; and at least partially separating the material from the substrate.

A method of removing a material on a surface of a substrate comprises contacting the material on the surface of the substrate with the above-described ketal adduct under removal conditions; and at least partially separating the material from the substrate, wherein 0 to 1 wt % of water is present during contacting.

The above described and other embodiments are further described in the drawings and detailed description that follow.

DETAILED DESCRIPTION

The inventors hereof have discovered that the ketal adducts of ketocarboxy esters, in particular levulinate esters, offer a combination of properties that are useful for stripping or removing materials from surfaces. Such stripping and removal compositions include formulations for paint stripping, graffiti removal, ink cleaning and removal, adhesive removal, mastic removal, photoresist removal, wax stripping, asphalt removal, concrete cleaning, form cleaning, mold cleaning hand cleaning, sap/pitch removal, oil stain cleaning and removing, parts degreasing, and engine degreasing. The varying solubilities of the ketal adducts makes them useful in a broad variety of compositions, particularly a broad variety of organic removal compositions. A further advantage is that certain of the ketal adducts, such as the levulinate ester ketals, can be derived from biological feedstocks.

The ketocarboxy ester ketals, which are sometimes referred to herein as "ketal adducts" have the general formula (1):

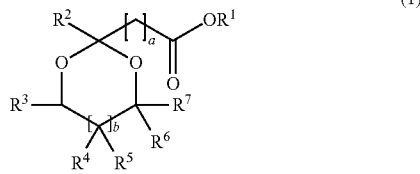

wherein
$R^1$ is C1-6 alkyl,
$R^2$ is hydrogen or C1-3 alkyl,
each $R^3$, $R^4$, and $R^5$ is independently hydrogen or C1-6 alkyl,
$R^6$ and $R^7$ are each independently hydrogen or C1-6 alkyl,
a=0-3, and
b=0-1.

More specifically, $R^1$ is C1-6 alkyl, $R^2$ is methyl, each $R^3$, $R^4$, and $R^5$ is independently hydrogen or C1-3 alkyl, $R^6$ is hydrogen or C1-6 alkyl, $R^7$ is hydrogen, a=1-3, and b=0-1.

Even more specifically $R^1$ is C1-4 alkyl, $R^2$ is methyl, $R^3$ is hydrogen, $R^6$ is hydrogen or C1-3 alkyl, $R^7$ is hydrogen, a=1-2, and b=0.

In a specific embodiment $R^1$ is C1-4 alkyl, $R^2$ is methyl, $R^3$ is hydrogen, $R^6$ is hydrogen, methyl, or ethyl, $R^7$ is hydrogen, a=2, and b=0.

Still more specifically, the ketal adduct is the 1,2-propanediol adduct of a levulinic acid ester, having formula (1a):

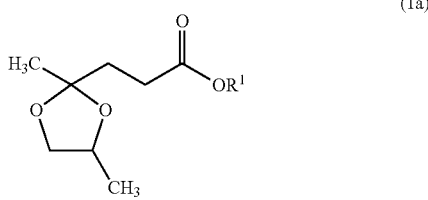

wherein $R^1$ is as defined above, specifically a C1-4 alkyl, more specifically ethyl or butyl. Ethyl levulinate propylene glycol ketal ("EtLPK") is obtained when $R^1$ is ethyl in formula (1a).

The ketal adducts of formula (1) can be obtained by the acid-catalyzed reaction of the corresponding ketoacid ester of formula (2) with a polyol of formula (3):

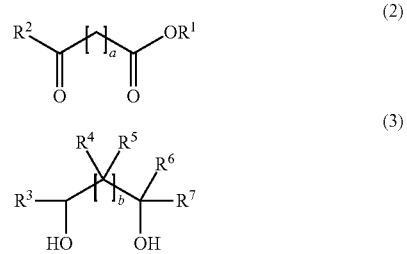

wherein each of $R^1$, $R^2$, $R^3$, $R^4$, $R^6$ and $R^7$, and a and b are as defined above. Reaction conditions are described in WO 09/032,905, for example. Many of the compounds falling within the scope of formulas (2) and (3) can be bio-sourced. The ketal adducts thus provide an entry point for a broad variety of bio-sourced solvents. For example, levulinic acid is produced by the thermochemical treatment of various carbohydrates such as cellulose; subsequent esterification with bio-sourced alkanols and ketalization of the levulinate ester with polyhydroxy compounds such glycerol or propylene glycol produces a bioderived solvent.

In a highly advantageous feature, selection of each of the specific $R^1$, $R^2$, $R^3$, $R^4$, $R^6$, and $R^7$ groups and a and b in the ketal adducts of formula (1) allows the chemical and physical properties of the ketal adducts to be adjusted to achieve the desired combination of properties, for example, solubilizing activity, and volatility. The ability to adjust each of these features using a single scaffold provides greater flexibility in designing solvents that achieve the technical requirements of the foregoing compositions.

Thus, in a specific embodiment each of the specific $R^1$, $R^2$, $R^3$, $R^4$, $R^6$, and $R^7$ groups and a and b are selected to provide a desired solubilizing activity, that is, the ability of the ketal adduct to solubilize a solute. The presence of ester and ether-like functionality allows interaction of the ketal adduct with a variety of solute functional groups.

The ketal adducts (1), specifically (1a), are further advantageous due to their low volatility, which can be especially desirable for paint and graffiti removal where rapid volatilization of the remover formulation necessitates re-application of the product. Volatility manifests itself in a number of key properties for solvents, including boiling point, vapor pressure, relative evaporation rate, flammability, odor, and volatile organic compound (VOC) content. The desired volatility profile of a solvent varies considerably by application, and there are often conflicting considerations. For instance, highly volatile process solvents require less energy to remove after use, but in many cases also require special handling due to higher flammability. Appropriate selection of each of the specific $R^1$, $R^2$, $R^3$, $R^4$, $R^6$, and $R^7$ groups and a and b can further provide a selected volatility. EtLPK in particular is of acceptably low volatility and low flammability.

As stated above, the ketal adducts (1), specifically (1a) are useful in paint stripping and graffiti removal compositions. The two types of compositions are related, as graffiti is often applied using paint. However, it has also been found that the ketal adducts are useful for the removal of adhesives, mastic, ink, photoresist, asphalt, pitch, grease, oil, and other types of coating. The ketal adducts have excellent combination of properties for use in these applications, including solubilizing activity, low flammability, long work times, biodegradability, non-corrosiveness, and low odor.

In an embodiment, the removal compositions contain only the ketal adduct (1), specifically (1 a), and 0 to 1% by weight of water, based on the total weight of the removal composition. In another embodiment, the removal compositions comprise the ketal adduct (1), specifically (1a); 0 to 1% by weight of water, based on the total weight of the removal composition; and one or more additional components, for example a cosolvent and/or other components as described in more detail below.

Exemplary cosolvents include:
aliphatic hydrocarbons, for example $C_{6-30}$ straight, branched-chain, or cyclic aliphatic hydrocarbons, that are preferably liquid at ambient temperatures and have a boiling point of at least about 100° C., e.g., mineral oil (also referred to as liquid petrolatum or liquid paraffin), mineral spirits (also referred to as ligroin or petroleum spirits), and low flashpoint cuts of hydrocarbon distillates (e.g., Conosol® C-145 (primarily of C10-13 cycloparaffinic and isoparaffinic hydrocarbons), Conosol® C-170 (composed primarily of C10-15 cycloparaffinic and isoparaffinic hydrocarbons), Conosol® C-200 (a composed primarily of C12-16 cycloparaffinic and isoparaffinic hydrocarbons), and Conosol® 215 (composed primarily of C12-15 cycloparaffinic and isoparaffinic hydrocarbons), from Calumet Specialty partners);

aromatic hydrocarbons, for example naphthalene, C1-8 alkyl derivatives of benzene, and C1-8 alkyl derivatives of naphthalene, specifically toluene, xylene (o, m, or p), cumene, ethyl benzene, mesitylene, durene, sec-amylbenzene, n-butylbenzene, naphthalene, and methyl naphthalene;

terpenes, for example, turpentine, alpha-pinene, beta-pinene, and d-limonene;

organic sulfur-containing compounds such as sulfoxides, for example dimethyl sulfoxide (DMSO);

chlorinated solvents, for example chlorinated C1-6 aliphatic compounds such as allyl chloride, carbon tetrachloride, chloroform, 1,1-dichloroethane, dichloroethylether, 1,2-dichloroethylene, dichloroisopropyl ether, ethyl chloride, ethylene dichloride, isopropyl chloride, methyl chloride, perchloroethylene, propylene dichloride, 1,1,2-trichloroethane, trichloroethylene 1,2,3 trichloropropene, and methylene chloride (dichloromethane, or DCM);

alcohols, for example amyl alcohol, n-butanol, 3-butoxyethyl-2-propanol, benzyl alcohol, benzyloxyethanol, diethoxyethanol, diisobutyl carbinol, dimethyl heptanol, ethanol, 2-ethylhexanol, ethylene glycol, glycerin, 1-hexanol, isobutanol, isopropanol, methanol, methyl amyl alcohol, 2-methyl-1-butanol, 1-pentanol, 1-propanol, propylene glycol, and 2,2,4-trimethyl-1,3-pentanediol monoisobutyrate (commercially available as UCAR FILMER™ IBT from Dow Chemical Co.);

glycol ethers, for example diethylene glycol methyl ether, diethylene glycol mono-n-butyl ether (commercially available as Butyl CARBITOL from Dow), diethylene glycol monoethyl ether (commercially available as CARBITOL from Dow), diethylene glycol monohexyl ether (commercially available as Hexyl CARBITOL from Dow), diethylene glycol monomethyl ether (commercially available as Methyl CARBITOL from Dow), diethylene glycol monopropyl ether (commercially available as Propyl CARBITOL from Dow), diethylene glycol n-butyl ether acetate (commercially available as Butyl CARBITOL™ Acetate from Dow), dipropylene glycol monobutyl ether (commercially available as DOWANOL™ DPnB from Dow), dipropylene glycol monomethyl ether (commercially available as DOWANOL DPM from Dow), dipropylene glycol monopropyl ether (commercially available as DOWANOL DPnP from Dow), dipropylene glycol tert-butyl ether, ethylene glycol methyl ether acetate (commercially available as Methyl CELLOSOLVE Acetate from Dow), ethylene glycol monobutyl ether (commercially available as Butyl CELLOSOLVE from Dow), ethylene glycol monohexyl ether (commercially available as Hexyl CELLOSOLVE from Dow), ethylene glycol monopropyl ether (commercially available as Propyl CELLOSOLVE from Dow), ethylene glycol n-butyl ether acetate (commercially available as Butyl CELLOSOLVE Acetate from Dow), ethylene glycol phenyl ether (commercially available as "DOWANOL™ EPh" from Dow), heptaethylene glycol monobenzyl ether, heptaethylene glycol monophenyl ether, hexaethylene glycol monobenzyl ether, hexaethylene glycol monophenyl ether, pentaethylene glycol monobenzyl ether, pentaethylene glycol monophenyl ether, propylene glycol ethyl ether, propylene glycol methyl ether acetate (commercially available as DOWANOL™ PMA from Dow), propylene glycol monobutyl ether (commercially available as DOWANOL PnB from Dow), propylene glycol monomethyl ether (commercially available as DOWANOL PM from Dow), propylene glycol monopropyl ether (commercially available as DOWANOL PnP from Dow), propylene glycol phenyl ether (commercially available as "DOWANOL PPh" from Dow), tetraethylene glycol monobenzyl ether, tetraethylene glycol monophenyl ether, triethylene glycol methyl ether, triethylene glycol monobenzyl ether, triethylene glycol monophenyl ether, tripropylene glycol methyl ether (commercially available as DOWANOL TPM from Dow), and tripropylene glycol n-butyl ether (commercially available as DOWANOL TPnB from Dow);

water-soluble ethoxylates of propylene glycol monophenyl ether (preferably, containing an average of at least 2 oxyethylene moieties per molecule);

water-soluble or water-dispersible polymeric amines such as poly(ethylene imine);

amides such as acetamidophenol, N,N-dimethyl formamide (DMF), and acetanilide, and cyclic amides such as 1-methyl-2-pyrrolidone (NMP), N-ethyl-2-pyrrolidone, N-isopropyl-2-pyrrolidone, N-cyclohexyl-2-pyrrolidone, 2-hydroxyethyl-2-pyrrolidone, N-dimethylaminopropyl-2-pyrrolidone, vinyl-pyrrolidone, and 2-pyrrolidone;

amines such as 2-(2-aminoethoxy)ethanol, 2-acetyl-1-methylpyrrole, 2-amino-2-methyl-1-propanolalkanolamines (e.g., n-butyldiethanolamine, diethanolamine, diisopropanolamine, dimethylethanolamine, ethanolamine, isopropanolamine, methylisopropanolamine, phenyl diethanolamine, and triethanolamine), cyclic amines (e.g., N-methylpyrrolidine, N-methylpyyrole, morpholine, and oxazolidines), n-butylaminoethanol, diethylaminoethanol, diglycolamine, 2-methylaminoethanol, and trialkylamines (e.g. triethylamine);

ketones and cyclic ketones such as isobutyl heptyl ketone, isophorone, methyl ethyl ketone, methyl isobutyl ketone, diisobutyl ketone, diacetone alcohol, acetophenone, methyl n-amyl ketone, cyclohexanone, and cycloheptanone;

dialkyl carbonates such as dimethyl carbonate, diethyl carbonate, dipropyl carbonate, diisopropyl carbonate, and dibutyl carbonate;

cyclic carbonates such as propylene carbonate and ethylene carbonate;

monoesters such as amyl acetate, benzyl acetate, benzyl benzoate, butyl acetate, ethyl acetate, ethyl propionate, ethyl lactate, isobutyl acetate, isopropyl acetate, n-butyl propionate, n-pentyl propionate, n-propyl acetate, n-propyl propionate, butyl lactate, the C1-4 alkyl esters of C6-22 saturated or unsaturated carboxylic acids, such as the methyl ester of C6-14 unsaturated fatty acids; the glycerol ester of fatty acids, including those derived from vegetable oils such as linseed, coconut, palm, soybean, cottonseed, groundnut, sunflower, rape, sesame, olive, corn, safflower, palm kernel, castor oil, peanut, fish, lard, mustard seed, poppyseed, turpentine, and tall oil, and ethyl 3-ethoxypropionate (commercially available as UCAR™ Ester EEP from Dow Chemical Co.);

dibasic esters such as dimethyl adipate, dimethyl succinate, dimethyl glutarate, dimethyl malonate, diethyl adipate, diethyl succinate, diethyl glutarate, dibutyl succinate, dibutyl glutarate and products available under the trade designations DBE™, DBE-3, DBE-4, DBE-5, DBE-6, DBE-9, DBE-IB, and DBE-ME from Invista; alkoxylated aromatic alcohols as described in U.S. Pat. No. 7,179,775, in particular the alkoxylated aromatic alcohols containing at least one aromatic ring per molecule and alkoxylate units of general formula —$(CR^1R^3$—$CR^2R^4$—$O)_n$—$R^5$ wherein: R', $R^2$, $R^3$, and $R^4$ are each independently hydrogen or methyl; $R^5$ is hydrogen, a C1-6 alkyl, or phenyl; and n is 2-10, wherein the alkoxylate units are attached to the aromatic ring directly or through an ether (oxygen) linkage or an oxymethylene (—$CHR^8O$—) linkage, wherein $R^8$ is hydrogen or $C_{1-4}$ alkyl. A combination comprising any one or more of the foregoing cosolvents can be used. In an embodiment, the cosolvent is NMP.

The ratio of ketal adduct to cosolvent can vary widely depending on the ketal adduct, the cosolvent, and the intended use, and can be from 1:99 to 99:1, specifically from 10:90 to 90:10, more specifically from 20:80 to 80:20, from 30:70 to 70:30, or from 40:60 to 60:40, all by volume.

The removal compositions can be formulated as, for example, a paint remover, graffiti remover, ink remover, adhesive remover, mastic remover, photoresist remover, wax remover, asphalt remover, concrete cleaner, form cleaner, hand cleaner, body cleaner, sap remover, oil remover, or grease remover. A single composition can have more than one use, for example a single composition can be used as both a paint and ink remover, as a paint, oil, and grease remover.

Thus, the removal compositions can contain other components to aid in the function of the compositions, for example abrasive particles, organic amine accelerators, organic acid accelerators, antioxidants, antirust additives, biocides, colorants, corrosion inhibitors, cosolvents, defoamers, dyes, enzymes, light stabilizers, odor masking agents (including perfumes), plasticizers, preservatives, surfactants (including amphoteric, anionic, cationic, nonionic, or zwitterionic), thickeners, and combinations comprising at least one of the foregoing. It is to be understood that a single additive can have more than one function, and that characterization of an additive as having that function (e.g., as a cosolvent) does not exclude the additive from performing another function. The concentrations of the individual additives of the removal compositions can be varied as depending upon components of the removal composition, the type of material to be removed, and the rate at which material removal is to be effected. Optimal concentrations for a particular application can be readily determined by a worker skilled in the art using standard experimental methods, and the guidelines provided below.

In a specific embodiment, the removal composition comprises an amide cosolvent, for example NMP, an amine accelerator, for example morpholine, a thickener, for example a cellulose thickener such as methylcellulose, and a surfactant.

In another specific embodiment, the removal composition comprises a sulfoxide cosolvent, for example dimethyl sulfoxide, an amine accelerator, for example morpholine, a thickener, for example a cellulose thickener such as methylcellulose, and a surfactant.

The organic amine accelerators can include those listed above as cosolvents. Accelerators are believed to accentuate the performance of the composition by chemically attacking the organic binder of the coating and thereby weakening the adhesion and cohesion of the coating. Exemplary amine accelerators include ethanolamine, diethanolamine, ethylenediamine tetraacetic acid, morpholine, triethanolamine, triethylamine, and 2-(N,N'-diethylamino)ethanol). When used as an additive, the amine accelerator can be present in an amount from 0.1 to 20 wt. %, or from 1 to 10 wt. %, although these amounts are merely illustrative.

Exemplary organic acid accelerators include C1-22 carboxylic acids (e.g., formic acid, acetic acid, propionic acid, oleic acid, oxalic acid, and hydroxyacetic acid). When used as an additive, the organic acid accelerator can be present in an amount from 0.1 to 20 wt. %, or from 1 to 10 wt. %, although these amounts are merely illustrative.

Corrosion inhibitors can be present, particularly where the composition is provided in a metal container, or when an acid accelerator is present. Corrosion inhibitors can be, for example, a molecule that has both an oil soluble portion and a water soluble portion, such as an amphoteric surfactant containing an amine functionality in an amount from about 0.05% to about 2% by weight, specifically about 0.25% to about 1.0%, such as the disodium N-lauryl iminodipropionate esters available as DERIPHAT® amphoteric surfactants from Cognis Corporation. Other corrosion inhibitors include amine soaps of fatty acids and fatty alkanolamides such as the $C_8$ to $C_{18}$ fatty alkanolamides, examples of which include STANDAMID® alkanolamides, available from Cognis Corporation. Such corrosion inhibitors can also be used for post-application anti-corrosion effects on surfaces that will rust or corrode because of the presence of water in the cleaning compositions, such as on metal surfaces such as iron and steel and the like.

The removal compositions can also contain an effective amount of odor masking agents, such as essential oils, aroma chemicals, perfumes, and the like, for example, ambergris, borneol and its esters, carvone, castoreum, civet, cinnamaldehyde, citrals, clove oil, galbanum, jasmine, limonene, linalool and its esters, pinenes (alphas, betas, etc.), rosemary oil, sandalwood, terpineols, terpinenes, and the like, benzaldehyde, benzoin, isoamyl acetate (banana); isobutyl propionate (rum); methyl anthranilate (grape); benzyl acetate (peach), dipentene, methyl butyrate (apple); ethyl butyrate (pineapple); octyl acetate (orange); n-propyl acetate (pear); ethyl phenyl acetate (honey), and the like. An effective amount of such odor masking agents will be readily determinable by those skilled in the art, and can be, for example, about 0.25% to about 2.50% by weight of the removal composition specifically about 0.4% to about 1.0%.

Exemplary plasticizers include phthalate esters, for example dibutyl phthalate, diethylhexyl phthalate, and diethyl phthalate; aliphatic diesters, for example dioctyl adipate; terephthalate esters, for example dioctyl terephthalate; citrate esters, for example acetyl triethyl citrate and acetyl tri-n-butyl citrate; ketal based plasticizers, such as those described in PCT Application WO 2010/151558, or a combination comprising at least one of the foregoing. When used, the plasticizer is present in an amount from about 0.1 to about 10 wt. %, based on the total weight of the removal composition.

A wide variety of surfactants can be utilized, depending on the application, and can be amphoteric, anionic, cationic, nonionic, or zwitterionic. A surfactant or combination of surfactants can be present in order to improve wetting of the coating to be removed and to hasten penetration of the active components. In addition, a surfactant can facilitate water rinsing and water clean-up of the substrate after removal of the coating. Exemplary amphoteric surfactants include amine oxide compounds having the formula RR'R"N→O wherein each R, R' and R" is independently a $C_1$-$C_{24}$ alkyl, aryl or arylalkyl group) that can optionally contain one or more P, O, S or N heteroatoms. Exemplary amphoteric surfactants also include betaine compounds of the formula RR'R"N$^+$(CH$_2$)$_n$C(O)O$^-$ wherein each R, R' and R" is independently a C$_1$-C$_{24}$ alkyl, aryl or arylalkyl group) that can optionally contain one or more P, O, S or N heteroatoms and n is about 1 to about 10. A combination comprising at least one of the foregoing can be used.

Exemplary anionic surfactants include the water-soluble salts of alkylbenzene sulfonates such as the isopropylamine salt of a C$_{10-14}$ alkyl benzene sulfonic acid, and/or a C$_{8-14}$ fatty alcohol sulfate, alkyl sulfates, alkyl polyethoxy ether sulfates, paraffin sulfonates, alpha-olefin sulfonates and sulfosuccinates, alpha-sulfocarboxylates and their esters, alkyl glyceryl ether sulfonates, fatty acid monoglyceride sulfates and sulfonates, alkyl phenol polyethoxyether sulfates, the water-soluble salts or esters of alpha-sulfonated fatty acids containing from about 6 to about 20 carbon atoms in the fatty acid group and from about 1 to about 10 carbon atoms in the ester group, and the like. When present, the anionic surfactant can be present in the composition in an amount from about 0.1 to about 15% by weight, from about 3 to about 12% by weight, and most preferably from about 5 to about 10% by weight, based on the weight of the composition. A combination comprising at least one of the foregoing can be used.

In addition to, or instead of an anionic surfactant, a short-chain surfactant can be present, for example C$_3$-C$_6$ alcohols, glycols, glycol ethers such as propylene glycol n-butyl ether, pyrrolidones, glycol ether esters, and the like. A combination comprising at least one of the foregoing can be used.

Exemplary cationic surfactants include quaternary amine compounds having the formula RR'R"R'"N$^+$X where each R, R', R" and R'" is independently a C$_1$-C$_{24}$ alkyl, aryl or arylalkyl group) that can optionally contain one or more P, O, S or N heteroatoms, and X is F, Cl, Br, I or an alkyl sulfate. A combination comprising at least one of the foregoing can be used.

Exemplary nonionic surfactants include alcohol ethoxylates (e.g., C$_6$-C$_{24}$ or C$_6$-C$_{16}$ alcohol ethoxylates) having 1 to about 20 ethylene oxide groups (e.g., about 9 to about 20 ethylene oxide groups), alkylphenol ethoxylates (e.g., C$_6$-C$_{24}$ or C$_8$-C$_{10}$ alkylphenol ethoxylates) having 1 to about 100 ethylene oxide groups (e.g., about 12 to about 20 ethylene oxide groups), alkylpolyglycosides (e.g., C$_6$-C$_{24}$ or C$_6$-C$_{20}$ alkylpolyglycosides) having 1 to about 20 glycoside groups (e.g., about 9 to about 20 glycoside groups). A combination comprising at least one of the foregoing can be used.

As a general guide, the amount of surfactant can be about 0.1 to about 20%, about 0.1 to about 15% or about 2 to about 15% of the total weight of the removal composition.

Thickeners can be present to adjust the rheological properties of the removal compositions. The removal of partially dried paint removal from automotive paint spray booths, for example, is generally performed by spraying a coatings remover onto the spray booth. The coatings remover must be thin enough to spray easily but must rapidly build in viscosity under low shear conditions to effectively cling to vertical surfaces. A higher viscosity formulation is generally desired if the coatings remover is to be painted on while a low viscosity formulation containing no added thickener is typically used where the coated substrate is to be soaked in a tank. Thickeners can also serve to increase the effectiveness of the coatings removers by decreasing the rate of evaporation of the volatile components after application to a coated substrate. Use of a thickener in the composition enables the composition to be applied onto vertical surfaces without any attendant dripping or run-off therefrom, and also inhibits dissipation of the composition into porous substrates such as brick or concrete.

Exemplary thickeners are natural or synthetic clays including bentonite, hectorite, smectite and other silicates such as available grades of BENTOLITET™, CLAYTONET™ and GELWHITE™ bentonites, PERMONT™ smectites, CLOISITE™ magnesium aluminum silicates, LAPONITET™ silicates and GARAMITE™ silicates (all available from Southern Clay Products, Inc.) and available grades of OPTIGELT™ bentonites, hectorites, smectites and other clays (all from Sued-Chemie Group); stearates of organoclay compounds such as tetraalkyl ammonium bentonite; gums and other polysaccharides such as carrageenan gum (e.g., GENUVISCO™ X-906-02 (from CP Kelco)), cassia gum, diutan gum (e.g., GEOVIS™ XT, KELCO-CRETE™ 80, KELCO-CRETE 200 and KOC617 (all from CP Kelco)), gellan gum (e.g., KELCOGEL™, KELCOGEL F and KELCOGEL LT 100 (all from CP Kelco)), guar gum, Gum Arabic, Gum Tragacanth, locust bean gum, whelan gum and Xanthan gum (e.g., KELZAN™, KELZAN AR, KELZAN ASX, KELZAN ASX T, KELZAN CC, KELZAN HP, KELZAN RD, KELZAN S, KELZAN ST, KELZAN T, KELTROL™, KELTROL T and KELTROL TF (all from CP Kelco) and VANZAN™ and VANZAN D (both from R.T. Vanderbilt Co.)); hydrocolloids such as NOVEGUM™ C865, NOVEGUM C866 and NOVEGUM G888 (all from Noveon, Inc.); alginates such as agar; cellulose ethers such as ethyl cellulose, hydroxyethyl cellulose, ethyl hydroxyethyl cellulose, methyl cellulose, hydroxypropyl cellulose, hydroxypropyl methyl cellulose, and other alkyl or hydroxyalkyl cellulose ethers, commercially available, e.g., as METHOCEL™ K15MDGSE, METHOCEL K4MDGSE, METHOCEL 311, METHOCEL F4M PRG and METHOCEL OS (all from Dow), XDS 8898.5 cellulose ether (from Dow), and KLUCEL™ H, KLUCEL M or KLUCEL G (all from Ashland, Inc.); acrylic acid homopolymers or copolymers, e.g., those which may be neutralized with a salt including associative or non-associative thickeners such as ACUSOL™ 801s, ACUSOL 810, ACUSOL 810A, ACUSOL 820, ACUSOL 823 and ACUSOL 830 acrylate polymers (all from Rohm & Haas Co.) or those which may be crosslinked (e.g., with a polyalkenyl polyether) including CARBOPOL™ 674, CARBOPOL 676, CARBOPOL ETD 2691, CARBOPOL ETD 2623, CARBOPOL EZ-3, CARBOPOL EZ-3A, CARBOPOL EZ-4 and CARBOPOL ULTREZ™ 21 (all from Noveon, Inc.); PEMULENT™ 1622 copolymer (from Noveon, Inc.); polyethylene oxides (e.g., high molecular weight polyethylene oxides) such as polyethylene glycols and methoxypolyethylene glycols; polyvinyl alcohols; polyvinyl pyrrolidone; starches; polyurethanes including RHEOLATE™ 266 (from Elementis Specialties, Inc.), and available grades of OPTIFLO™ associative thickeners (all available from Sud-Chemie Group); and methyl vinyl ether/maleic anhydride copolymers. Other possible thickeners include hydrophobe-modified ethoxy urethane (HEUR) thickeners, hydrophobe-modified alkali soluble emulsion (HASE) thickeners, hydrophobe-modified hydroxyethyl cellulose (HM-HEC) thickeners, and HEUR-ASE combination thickeners. A combination comprising at least one of the foregoing can be used.

The thickener can be used in an amount from about 0.1 to about 30 wt. %, specifically about 2 to about 20 wt. %, and most specifically about 3 to about 10 wt. %, based on the total weight of the removal composition.

A method of preparing a removal composition comprises combining the ketal adducts (1), specifically (1a) and any cosolvent or other component to form the removal composition. The ketal adducts and additives can be added in any suitable order to the additional component(s) present in the composition, for example a thickener and an amide cosolvent to provide these additives in the removal composition.

When used with cosolvents or other components, the removal compositions can be provided as a concentrate. The concentrates are usually diluted in water for use as a working water-based removing composition. In an embodiment, a two-part concentrate package can be provided which typically comprises a Part A and a Part B, where each part contains a component likely to react with the other part, for example the ketal and an amine in Part A and an inorganic base in Part B.

The removal compositions can alternatively be formulated in other forms useful for removal or cleaning compositions, for example gels, wipes, aerosols, and the like. The removal compositions can be formulated in gel form by the addition of an effective amount of a gelling agent such as fumed silica, organic gums, polymers, copolymers, paraffin wax, bentonite clay, and cellulose ethers such as methyl cellulose and hydroxypropyl methyl cellulose commercially available as METHOCEL® cellulose ethers, from Dow Chemical. Wipes are generally a natural or synthetic fabric piece impregnated with the gel or liquid removal composition. When used as an aerosol, the removal formulations are formulated under pressure with a propellant as is known in the art.

A method of removing a material from a substrate comprises contacting the material with a composition comprising ketal adduct (1), specifically (1a) under conditions that effect removal, for example for a time effective to dissolve and/or lift the material; and separating the dissolved and/or lifted material from the substrate. As used herein, "dissolved" includes partial dissolution of a material, often referred to as softening, such that the material can be further removed from the substrate by rinsing or mechanical action. Of course, the removal composition can also be at least partially removed by separating the material.

The removal compositions can be used to remove a wide variety of materials, generally those soluble or softenable by organic solvents. Examples include materials such as inks for all types of substrates, including paper, wood, plastic, metal, textiles, ceramics, stone, skin, and for indoor or for outdoor use; adhesives and sealants, for example silicone, polyurethane, epoxy, polyvinyl acetate (including copolymers with ethylene), phenolic, amino resin, cyano acrylate, polyester, polyamide, rubber (styrene-butadiene and natural) or acrylic adhesives and sealants; mastics; photoresists; waxes, for example floor wax or bees wax; asphalts; saps (which as used herein includes pitches, rosins, tars, and natural resins such as tree sap); residual materials left in forms or molds, for example polymers such as alkyds, polyacetals, polyacrylates, polyacrylics, polyamides, polycarbonates, polyesters, polyethers, polyethylenes, polyimides, polystyrenes, polyurethanes, polyvinyls, silicones, natural and synthetic rubbers, and the like, and polymer additives; greases, for example silicone and petroleum-based greases; oils, including machine oil; and paints, finishes, and other coatings, for example, alkyd enamels, acrylic enamels, polyesters, polyurethanes, epoxy resin coatings, latex paints, oil-base paints, shellacs, phenolic coatings, gum varnishes, silicone coatings, polyvinyls, polyvinyl cinnamates, polyamides, polyimides, polyalkyl acrylates, polyalkyl methacrylates, drying oils, polyvinyl acrylates, and cellulosic resins.

The materials can be removed from surfaces that are reasonably resistant to the removal compositions, including natural and synthetic fabrics, wood, cardboard, and coated paper, especially if treated with a wax or other protective material, glass, thermoset resins, thermoplastic resins, ceramic, stone, masonry substrates, cement, or metals (e.g., aluminum alloys, zinc alloys, stainless steel, or galvanized steel). The removal compositions can further be used to a part of the human body, for example hands or hair, as well as animals.

Although the methods of contacting the surface with the removal composition can be accomplished in a number of ways, for example, in aerosol form or other spraying means such as by standard spray nozzles; brush application; dipping; coating; application in gel form such as from a squeeze bottle or brush, and the like, bit immersion and spraying can be specifically mentioned. If the surface to be cleaned is readily accessible, then spraying can be used. The spraying pressure will usually be from 1.3 bars to 8.0 bars absolute pressure. The mechanical force of the impinging removal composition facilitates removal of the material. On the other hand, if the surface to be cleaned has recesses or other shapes that are not readily accessible, immersion can be used. Of course, both methods can be used in combination and/or varied in ways apparent to those skilled in the art. During or after contacting, mechanical action, such as scraping, peeling, rubbing, wiping, and the like can be employed to increase contact and/or aid in dissolution and/or lifting.

The contact time needed to produce an effective degree of dissolution and/or lifting of the material from a surface will depend on the nature and thickness of the material, the composition of the removal composition, including the ingredient concentrations, the temperature of the composition, and other factors. With some materials and under some conditions, contact times of a few minutes (e.g., 2-3 minutes) can be sufficient. Operating temperature when using the removal compositions can be from 0 to 180° C. or higher, specifically 15 to 90° C., or 21 to 55° C. The treatment is most conveniently carried out at ambient temperature, but lift time may be shortened as desired by heating the coatings remover and/or substrate. Heating can be achieved by local application of heat such as with a heat gun, or more general application of heat, such as with an electric heater, infrared heater, and the like. It is to be understood however, that those skilled in the art can determine optimal conditions for particular removal applications by minimal experimentation. Higher temperatures generally increase the rate at which the material is removed from the surface.

Separating the ketal adduct and dissolved material from the substrate can include mechanical action, such as scraping, peeling, rubbing, wiping, and the like, or rinsing the substrate with additional removal composition or another solvent, including water or aqueous mixture of water with an organic solvent.

The removal compositions described herein can accordingly be formulated for a wide variety of uses, such as paint removal (including cleaning and stripping), graffiti removal, ink removal, adhesive removal, mastic removal, photoresist removal, wax removal (including wax stripping), asphalt removal, concrete cleaning, form cleaning, mold cleaning, hand cleaning, sap removal, oil removal (including cleaning oil stains), degreasing (including parts degreasing and engine degreasing).

The following non-limiting examples further illustrate various embodiments of the invention.

EXAMPLES

Example 1

Ethyl levulinate glycerol ketal ("EtLGK", wherein $R^1$ and $R^2$ are methyl, a=2, b=0, $R^6$ is hydrogen, and $R^7$ is hydroxymethylene in Formula (1)) and EtLPK are characterized and compared with various known solvents in this example, in particular ethylene glycol butyl ether (EGBE), dipropylene glycol methyl ether (DPM), propylene glycol methyl ether acetate (PMA), dibasic esters (DBE), d-Limonene (DL), and soy methyl esters (SME).

Solubility studies with various polymers show the solvating effectiveness of the ketal adducts (1), specifically (1a). In these experiments, solubility observations were made after 0.5 g resin and 4.5 g solvent were agitated for 24 hours at room temperature. Solubility ratings ranged from 1 (complete solubility) to 6 (no effect) based on visual observations.

TABLE 1

|  | EGBE | DPM | PMA | DBE | DL | SME | EtLGK | EtLPK |
|---|---|---|---|---|---|---|---|---|
| Paraloid B-72 | 1 | 1 | 1 | 1 | 4 | 5 | 2 | 1 |
| Paraloid B-82 | 1 | 1 | 1 | 1 | 3 | 6 | 2 | 1 |
| Desmocoll 176 | 4 | 4 | 1 | 2 | 5 | 4 | 4 | 2 |
| Desmocoll 406 | 3 | 2 | 1 | 1 | 4 | 5 | 4 | 2 |
| CAP-482-0.5 | 2 | 2 | 1 | 1 | 6 | 6 | 2 | 1 |
| D.E.R.661 | 1 | 1 | 1 | 1 | 5 | 5 | 2 | 1 |
| EPON 1001F | 1 | 1 | 1 | 1 | 5 | 3 | 1 | 1 |
| PKHH | 1 | 1 | 2 | 1 | 6 | 6 | 5 | 1 |
| Butvar B-76 | 1 | 1 | 1 | 1 | 4 | 4 | 3 | 2 |
| Polyvinyl Acetate | 3 | 1 | 1 | 1 | 6 | 6 | 2 | 1 |

Solubility was based on visual observation of the solvent-polymer mixture using the following rating scheme:
1 = completely soluble, 2 = almost soluble, 3 = strongly swollen/slightly soluble, 4 = swollen, 5 = little swelling, 6 = no visible effect.
Resins tested were thermoplastic acrylics Paraloid B-72 and B-82 (Rohm and Haas Company), flexible polyurethanes Desmocoll 176 and 406 (Bayer Material Science LLC), cellulose acetate propionate CAP-482-0.5 (Eastman Chemical Company), solid epoxies D.E.R. 661 (The Dow Chemical Company) and EPON 1001F (Momentive Specialty Chemicals Inc.), phenoxy PKHH (InChem Corporation), polyvinyl butyral Butvar B-76 (Solutia, Inc.), and polyvinyl acetate (Sigma-Aldrich Corporation)

The data in Table 1 shows that EtLPK dissolves a variety of common polymers, unexpectedly outperforming EtLGK, and with performance similar to petroleum-based solvents ethylene glycol butyl ether (EGBE), dipropylene glycol methyl ether (DPM), propylene glycol methyl ether acetate (PMA), and dibasic esters (DBE). Both EtLGK and EtLPK significantly outperformed the bio-sourced solvents soy methyl esters (SME) and d-limonene (DL) in their ability to dissolve common polymers.

Hildebrand solubility parameters were determined from the heat of vaporization and molar volume of each of EtLGK and EtLPK. The Hildebrand numbers for EtLGK and EtLPK were determined and are shown in Table 2. The higher value for EtLGK reflects the presence of a hydroxyl group.

TABLE 2

| Solvent | Hildebrand Solubility Parameter ($MPa^{1/2}$) |
|---|---|
| EtLGK | 18.6 |
| EtLPK | 16.9 |

Table 3 shows the flammability of EtLGK, EtLPK, ethanol, propylene glycol methyl ether (PM), and ethylene glycol butyl ether (EGBE). Table 3 also shows the status of these compounds under the low vapor pressure (LVP) criteria established by the California Air Resources Board (CARB), which limit the total VOC content in consumer and institutional cleaning products, as well as certain personal care products and automotive aftercare products.

TABLE 3

| Volatility Profile | Ethanol | PM | EGBE | EtLGK | EtLPK |
|---|---|---|---|---|---|
| Non-Flammable? | NO | YES | YES | YES | YES |
| CARB LVP Exempt? | NO | NO | NO | YES | YES |

*California Environmental Protection Agency Air Resources Board, CARB LVP exemption criteria (2010).

The data in Table 3 show that EtLGK and EtLPK are not flammable and have high enough boiling points to meet the criteria for the low vapor pressure exemption from CARB's regulations for consumer products. Ethanol and common glycol ethers cannot meet the CARB LVP exemption criteria.

The volatility of EtLPK, EtLGK, and EtLGK-acetate (wherein $R^1$ and $R^2$ are methyl, a=2, b=0, $R^6$ is hydrogen and $R^7$ is —$CH_2OC(O)CH_3$) in Formula (1)) was tested relative to 2,2,4-trimethyl-1,3-pentanediol monoisobutyrate ("TEXANOL", available under the trademark TEXANOL from Eastman) as shown in Table 4. Volatility was determined at 110° C. in open TGA pan.

TABLE 4

|  | Relative Volatility (TEXANOL = 1) |
|---|---|
| TEXANOL | 1.0 |
| EtLGK | 0.15 |
| EtLGK acetate | 0.20 |
| EtLPK | 1.50 |

The data in Table 4 show that EtLGK acetate is only slightly more volatile than EtLGK (relative volatility vs. TEXANOL=0.20), while EtLPK is more volatile than Texanol (relative volatility vs. TEXANOL=1.5).

Example 2

EtLGK and EtLPK were tested as alternatives to DBE in graffiti removal formulations. The neat solvents were compared in their ability to remove graffiti by the TURI lab at the University of Massachusetts—Lowell. In each test, one set of stainless steel and wood coupons were coated with Dayetek Daye Black quick dry lithographic ink using a hand held swab; a second set of stainless steel and wood coupons were coated with Barnes Group Bowman Distribution Industrial Finish Gloss Black spray paint No 24700. Coated coupons were allowed to sit for several hours for drying of applied ink/paint.

In the first test, three coupons were placed into a Gardner Straight Line Washability unit. A Kimberly-Clark Wypal reinforced paper towel was attached to the cleaning sled and soaked with 5-7 sprays of removal solutions. Each coupon was sprayed 7-10 times with the same cleaning removal solution (EtLGK, EtLPK, a 50:50 blend of EtLGK and EtLPK, and DBE). The cleaning unit was run for 20 cycles (~33 seconds). At the end of cleaning, visual observations were made and the coupons were ranked from best to worst for each of the cleaning solvents. Results are shown in Table 5.

TABLE 5

| Solution | Substrate | Cont | Rank 1 | Rank 2 | Rank 3 | Ave | Observations |
|---|---|---|---|---|---|---|---|
| EtLGK | Steel | Ink | 2 | 2 | 2 | 2.0 | ~75% removal |
| EtLPK | | | 1 | 1 | 1 | 1.0 | Almost full removal |
| 50:50 mix | | | 4 | 4 | 4 | 4.0 | >25% removal |
| DBE | | | 3 | 3 | 3 | 3.0 | >50% removal |
| EtLGK | Steel | Paint | 3 | 3 | 4 | 3.3 | Little removal; ink breakdown visible |
| EtLPK | | | 2 | 2 | 2 | 2.0 | Some removal; no breakdown |
| 50:50 mix | | | 1 | 1 | 1 | 1.0 | Partial removal; some ink breakdown |
| DBE | | | 4 | 4 | 3 | 3.7 | Significant residue |
| EtLGK | Wood | Ink | 3 | 3 | 3 | 3.0 | >50% removal; still some residue |
| EtLPK | | | 1 | 1 | 1 | 1.0 | Little residue; little staining |
| 50:50 mix | | | 4 | 4 | 4 | 4.0 | ~50% removal; residue; staining |
| DBE | | | 2 | 2 | 2 | 2.0 | >75% removal; little staining; some residue |
| EtLGK | Wood | Paint | 1 | 1 | 1 | 1.0 | Little removal; some staining; no breakdown |
| EtLPK | | | 4 | 2 | 3 | 3.0 | Little residue; lots of staining |
| 50:50 mix | | | 3 | 3 | 3 | 3.0 | More visible removal; staining |
| DBE | | | 2 | 4 | 2 | 2.7 | Residue; staining |

The spray paint was the easier of the two contaminants to be removed using 30 seconds of manual cleaning. Both the ketals solvents were ranked high for the ink removal from stainless steel. The EtLPK was ranked as the most effective of the four solvents for both surfaces for ink removal. According to the visual test, EtLPK was particularly effective at removing the ink.

In the second test, the same procedure was used as in the first experiment, except the coupons were judged gravimetrically—the coupons were weighed prior to cleaning to get the initial weight, and then weighed again after cleaning. Table 6 shows the amount of soil added, the amount remaining and the efficiency for each coupon, using EtLGK, EtLPK, a 50:50 blend of EtLGK and EtLPK, and DBE. Gravimetric analysis was inconclusive for both soils from the wood coupons due to weight gain in the final "clean" weights; therefore only the stainless steel results are shown in Table 6.

TABLE 6

| | Ink | | | % Removed | |
|---|---|---|---|---|---|
| Stainless Steel | 1 | 2 | 3 | Avg | St. dev |
| EtLGK | 43.02 | 42.97 | 43.89 | 43.3 | 0.5 |
| EtLPK | 93.02 | 78.83 | 39.80 | 70.6 | 27.6 |
| 50:50 mix | 88.31 | 88.98 | 83.94 | 87.1 | 2.7 |
| DBE | 92.69 | 88.17 | 93.28 | 91.4 | 2.8 |

| | Paint | | | % Removed | |
|---|---|---|---|---|---|
| Stainless Steel | 1 | 2 | 3 | Avg | St. dev |
| EtLGK | 26.81 | 35.68 | 15.29 | 25.9 | 10.2 |
| EtLPK | 85.25 | 92.45 | 94.44 | 90.7 | 4.8 |
| 50:50 mix | 50.30 | 35.47 | 64.41 | 50.1 | 14.5 |
| DBE | 89.43 | 93.72 | 73.55 | 85.6 | 10.6 |

For ink, DBE gave the highest value for percent removed, whereas EtLPK gave the highest value for paint removal, but in both cases standard deviations were sufficiently large to make solid conclusions difficult.

A third test was run by the same procedure as above, except the cleaning unit was run until the coupons were completely cleaned or when no additional contaminant was removed from the surface (as determined by viewing the paper towel condition after at least 40 cycles); the total number of cycles was recorded. Cycle numbers for each solvent are shown in Table 7.

TABLE 7

| Solvent | Substrate | Contaminant | # Cycles | Rank |
|---|---|---|---|---|
| EtLGK | Stainless Steel | Ink | 77 | 4 |
| EtLPK | | | 22 | 1 |
| 50:50 mix | | | 35 | 3 |
| DBE | | | 31 | 2 |
| EtLGK | Stainless Steel | Paint | 40 | 4 |
| EtLPK | | | 21 | 1 |
| 50:50 mix | | | 39 | 3 |
| DBE | | | 25 | 2 |
| EtLGK | Wood | Ink | 100 | 4 |
| EtLPK | | | 85 | 2 |
| 50:50 mix | | | 88 | 3 |
| DBE | | | 80 | 1 |
| EtLGK | Wood | Paint | 53 | 4 |
| EtLPK | | | 39 | 2 |
| 50:50 mix | | | 50 | 3 |
| DBE | | | 37 | 1 |

In this case, EtLPK needed the least number of total cycles for cleaning both the ink and paint from the stainless steel. DBE performed best on wood, although none of the products removed all of the paint from the wood surfaces—both the ink and paint left visual traces on in the grain of the wood. Overall, EtLPK and DBE had similar number of cycles required to reach the end point.

Example 3

EtLPK was formulated into NMP-based paint stripper A shown in Table 8.

TABLE 8

| Components | Weight |
|---|---|
| EtLPK | 45.0 |
| Mecellose 9860 (thickener) | 1.5 |

TABLE 8-continued

| Components | Weight |
|---|---|
| N-methyl pyrrolidone (NMP) | 50.0 |
| Morpholine | 1.0 |
| Ethylene glycol monobutyl ether | 2.5 |

The paint stripper formulation A of Table 8 was compared to a commercial product B, Zinsser Magic Strip Citrus-Action Gel, which contains NMP, dibasic esters, and ethanolamine (specific quantities are not known). The paint stripper formulations were tested on acrylic, alkyd, and polyurethane coatings using the protocol described in ASTM D6189. The test results are shown in Table 9.

TABLE 9

| Coating Type | Substrate | Stripper | % Coating Removal 15 min contact | % Coating Removal 30 min contact | Substrate Condition 15 min contact | Substrate Condition 30 min contact |
|---|---|---|---|---|---|---|
| Acrylic Paint, waterborne[1] | metal | B* | 25 | 100 | NA | 3-slight pitting |
| | metal | A | 50 | 100 | NA | 3-slight pitting |
| | wood | B* | 50 | 75 | NA | NA |
| | wood | A | 50 | 100 | NA | 5-no effect |
| Alkyd Paint, solvent-borne[2] | metal | B* | 10 | 10 | NA | NA |
| | metal | A | 25 | 25 | NA | NA |
| | wood | B* | 50 | 50 | NA | NA |
| | wood | A | 75 | 100 | NA | 5-no effect |
| Polyurethane Stain, solvent-borne[3] | metal | B* | 25 | 25 | NA | NA |
| | metal | A | 25 | 25 | NA | NA |
| | wood | B* | 25 | 75 | NA | NA |
| | wood | A | 50 | 100 | NA | 4-slightly rough |

[1]Behr Premium Plus Interior Satin Enamel
[2]Rust-Oluem Painter's Touch Satin Spray
[3]MinWax Fast-drying Polyurethane
*Comparative
NA—not applicable; coating not fully removed The data in Table 9 show that in almost all cases, the stripper formulation A in accordance with the present invention outperformed the comparative commercial product B.

Example 4

EtLPK was formulated as a pound-for-pound replacement of DBE and soy methyl esters in a paint stripper formulation to remove the confounding effects of different ingredients and levels as shown in Table 10. Methocell 311 was used as the thickener instead of Mecellose 9860 (Table 14). Results are shown in Table 11.

TABLE 10

| Components | Weight |
|---|---|
| Solvent (EtLPK, DBE, or soy methyl ester) | 45.0 |
| Methocell 311 (thickener) | 1.5 |
| N-methyl pyrrolidone (NMP) | 50.0 |
| Morpholine | 1.0 |
| Ethylene glycol monobutyl ether | 2.5 |

TABLE 11

| Coating Type | Substrate | Solvent | % Coating Removal 30 min contact | Substrate Condition 30 min contact |
|---|---|---|---|---|
| Acrylic Paint, waterborne[1] | metal | EtLPK | 75 | NA |
| | metal | DBE | 100 | 5-no effect |
| | metal | SME | 25 | NA |
| | wood | EtLPK | 100 | 5-no effect |
| | wood | DBE | 100 | 5-no effect |
| | wood | SME | 50 | NA |
| Alkyd Paint, solvent-borne[2] | metal | EtLPK | 50 | NA |
| | metal | DBE | 25 | NA |
| | metal | SME | 10 | NA |
| | wood | EtLPK | 25 | NA |
| | wood | DBE | 50 | NA |
| | wood | SME | 25 | NA |

NA—not applicable

EtLPK shows better performance than soy methyl esters in the common formulated paint stripper system. A comparison of EtLPK versus DBE showed superior results in one case, equivalent results in one case, and inferior results in two cases.

Example 5

A black ultraviolet-curable printing ink (Kolorcure Series 7500 Super Dense Black UV curable printing ink) was applied to aluminum mill finish and ground steel Q-panels (cleaned with acetone and paper towel) with a 1 mil (0.025 mm) draw down bar and cured for 10 minutes in a Loctite Zeta 7401 UV chamber with 400W metal halide bulb. A comparative solvent formulation (Soy-Sol 2300) and EtLPK were applied by brush in a 2-inch (51 mm) stripe to the aluminum panel. After 2.5 hours, EtLPK easily removed the coating with a 2-inch (51 mm) plastic putty knife while Soy-Sol only removed 10% of the coating over the contact area. The same test was repeated on the steel-coated panels. After 5 hours, EtLPK removed 50% of the coating in the contact area, while Soy-Sol removed 0% of coating in the contact area.

Example 6

1.33 grams of a sample of an uncured black printing ink (Lancer Group Excalibur Direct Print 500 Black, which is a heat cure formulation) was placed into three separate 20-mL scintillation vials. To each of the vials was added 10 grams of EtLPK, DBE, or Soy-Sol 2300 solvent composition, respectively. The vials were capped and mechanically shaken until dissolved. All solutions turned a cloudy black. EtLPK dissolved the sample completely within 60 minutes while 10% of the sample remained in the vial containing Soy-Sol 2300 and 50% remained in the vial containing DBE at 60 minutes mix time.

Example 7

EtLPK, d-limonene, and Steposol SB-W (soy methyl ester) were compared in their ability to remove an ultra violet (UV)-cured ink. Kolorcure 7500 (75-112) Super Dense Black UV-curable printing ink was applied over a standard vinyl floor tile using a drawdown bar at 1 mil (1.02 mm) wet film. The film was cured for 3 minutes using UV light in a Loctite Zeta 7401. The solvent was soaked into a cheesecloth that was affixed to the round side of a 16 oz ball-peen hammer. The hammer was attached to a motor that moved the hammer back and forth in a 3-inch (7.62 cm) stroke. The total number of double rub strokes was counted until the white tile showed through the removed black ink. Results are shown in Table 12.

TABLE 12

| Run | Solvent | Double Rubs |
|---|---|---|
| 1 | Deionized water | 500+ |
| 2 | EtLPK | 92 |
| 3 | d-limonene | 133 |
| 4 | Soy methyl ester | 148 |

The results show that EtLPK has an advantage in removing UV ink versus other solvents and the control of water.

Example 8

A caulk (Loctite Polyseamseal All Purpose Adhesive Caulk (Henkel)) was applied to 4-inch×1-inch (10.16 cm×2.54 cm) steel panels by manually wiping the adhesive onto the panel with a latex glove and curing at room temperature for 24 hours. The coated panels were then dipped into a solution of 90 wt % EtLPK and 10 wt % Tomadol 25-9 surfactant solution under constant agitation using a stir bar that rotated at 280 rpm. The coated panels soaked in the agitated solution for 1, 2, 4, and 8 hours. At each interval, 1 panel from each solution was pulled out and wiped with a cloth to see how much of the adhesive was removed, as noted in the following table. A comparative example was also carried out using a mixture of 45% d-limonene/45% Steposol SB-W/10% Tomadol 25-9. Results are shown in Table 13.

TABLE 13

| Run | Solvent | Wash Cycle (hr) | Observation |
|---|---|---|---|
| 1A | EtLPK | 1 | softened. 20% removal |
| 1B | EtLPK | 2 | softened. 35% removal |
| 1C | EtLPK | 4 | delamination. 100% removal |
| 1D | EtLPK | 8 | heavy delamination. 100% removal |
| 2A | d-limonene/soy methyl ester | 1 | no softening or removal |
| 2B | d-limonene/soy methyl ester | 2 | no softening or removal |
| 2C | d-limonene/soy methyl ester | 4 | no softening or removal |
| 2D | d-limonene/soy methyl ester | 8 | no softening or removal |

The results show that EtLPK performed better than the d-limonene/soy methyl ester/Tomadol solution at all time intervals for the adhesive caulk. The final film after 8 hours of soak with d-limonene/soy methyl ester showed no softening or signs of delamination.

Example 9

An adhesive (Liquid Nails, Small Project Repair Adhesive (Akzo Nobel)) was applied to 4-inch by 1-inch (10.16 cm×2.54 cm) steel panels by manually wiping the adhesive onto the panel with a latex glove and curing at room temperature for 24 hours. The coated panels were then dipped into a solution of 90 wt % EtLPK and 10 wt % Tomadol 25-9 surfactant solution under constant agitation using a stir bar that rotated at 280 rpm. The coated panels soaked in the agitated solution for 1, 2, 4, and 8 hours. At each interval, 1 panel from each solution was pulled out and wiped with a cloth to see how much of the adhesive was removed, as noted in the following table. A comparative example was also carried out using a mixture of 45% d-limonene/45% Steposol SB-W/10% Tomadol 25-9. Results are shown in Table 14.

TABLE 14

| Expt | Solvent | Wash Cycle (hr) | Observation |
|---|---|---|---|
| 1A | EtLPK | 1 | complete removal |
| 1B | EtLPK | 2 | complete removal |
| 1C | EtLPK | 4 | complete removal |
| 1D | EtLPK | 8 | complete removal |
| 2A | d-limonene/soy methyl ester | 1 | no rub off |
| 2B | d-limonene/soy methyl ester | 2 | slight softening but no rub off |
| 2C | d-limonene/soy methyl ester | 4 | slight softening but no rub off |
| 2D | d-limonene/soy methyl ester | 8 | slight softening but no rub off |

EtLPK performed better than the d-limonene/soy methyl ester/Tomadol solution at all time intervals for the adhesive. The final film after 8 hours of soak with d-limonene/soy methyl ester showed minimal signs of delamination and, even when scraping, was still difficult to remove from the metal substrate.

Example 10

PowerGrab All-Purpose Construction Adhesive by Loctite (Henkel) was applied to 4-inch by 1-inch steel panels by manually wiping the adhesive onto the panel with a latex glove and curing at room temperature for 24 hours. The coated panels were then dipped into a solution of 90 wt % EtLPK and 10 wt % Tomadol 25-9 surfactant solution under constant agitation using a stir bar that rotated at 280 rpm. The coated panels soaked in the agitated solution for 1, 2, 4, and 8 hours. At each interval, 1 panel from each solution was pulled out and wiped with a cloth to see how much of the adhesive was removed, as noted in the following table. A comparative example was also carried out using a mixture of 45% d-limonene/45% Steposol SB-W/10% Tomadol 25-9. Results are shown in Table 15.

TABLE 15

| Run | Solvent | Wash Cycle (hr) | Observation |
|---|---|---|---|
| A1 | EtLPK | 1 | softened but no rub off |
| A2 | EtLPK | 2 | softened but no rub off |
| A3 | EtLPK | 4 | softened and 25% rub off |
| A4 | EtLPK | 8 | softened and 35% rub off |
| B1 | d-limonene/soy methyl ester | 1 | softened but no rub off |
| B2 | d-limonene/soy methyl ester | 2 | softened but no rub off |
| B3 | d-limonene/soy methyl ester | 4 | softened but no rub off |
| B4 | d-limonene/soy methyl ester | 8 | softened and 35% rub off |

The Et LPK/Tomadol solution performed similarly to the d-limonene/soy methyl ester/Tomadol solution. In both cases, the adhesive was soft enough to scrape off but did not come off with wiping with a towel.

Example 11

EtLPK and Steposol SB-W (soy methyl ester) were compared in their ability to remove wax coatings. A wax (All-Wax Floor Wax by Lundmark Wax) was combined with a pigment (Sid Richardson Black pigment SR-630) and ground using sand to disperse the black pigment. The colored wax solution was applied over a standard vinyl floor tile using a drawdown bar at 1, 2, and 3 mil (0.025, 0.055, and 0.076 mm) wet film and was allowed to try overnight. The solvent was then soaked into a cheese cloth that was affixed to the round side of a 16-oz (0.45 kg) ball-peen hammer. The hammer was attached to a motor that moved the hammer back and forth in a 3-inch (7.6 cm) stroke. The total number of double rub strokes was counted until the white tile showed through the removed black wax. Results are shown in Table 16.

TABLE 16

| Wax Thickness, mil (mm) | Solvent | Double Rubs |
|---|---|---|
| 1 (0.025) | EtLPK | 14 |
| 2 (0.055) | EtLPK | 20 |
| 3 (0.076) | EtLPK | 24 |
| 1 (0.025) | DI water | 273 |
| 1 (0.025) | d-limonene | 6 |
| 2 (0.055) | d-limonene | 8 |
| 3 (0.076) | d-limonene | 9 |
| 1 (0.025) | Soy methyl ester | 25 |
| 2 (0.055) | Soy methyl ester | 28 |
| 3 (0.076) | Soy methyl ester | 33 |

In a related example, a wax (SC Johnson Paste Wax) was combined with a pigment (Sid Richardson Black pigment SR-630) by mixing in a vial by hand with a tongue depressor. The colored wax solution was applied over the tile using a towel at uniform thickness and was allowed to dry overnight. The solvent was soaked into a cheese cloth that was affixed to the round side of a 16-oz (0.45 kg) ball-peen hammer. The hammer was attached to a motor that moved the hammer back and forth in a 3-inch (7.6 cm) stroke. The total number of double rub strokes was counted until the white tile showed through the removed black wax. Results are shown in Table 17.

TABLE 17

| Run | Solvent | Double Rubs |
|---|---|---|
| 1 | EtLPK | 18 |
| 2 | DI water | 227 |
| 3 | d-limonene | 9 |
| 4 | Steposol SB-W | 26 |

The results in Tables 16 and 17 show that the EtLPK is effective in removing wax.

Example 12

Pine tar pitch removal was performed using EtLPK, d-limonene, and Steposol SB-W (soy methyl ester). Pine tar pitch obtained from Jas Townsend and Son was melted by heating to 85° C. and then applied to glass slides with a sponge brush. The resulting coated slide, after cooling overnight, was inserted into the beaker containing the experimental solvent. The slides were removed at 90 and 180 minutes and were evaluated for pitch removal by amount of total residual with and without wiping. Results are shown in Table 18.

TABLE 18

| Run | Solvent | Soak Time (min) | Observation |
|---|---|---|---|
| 1 | EtLPK | 90 | softened. 50% removal |
| 2 | d-limonene | 90 | 100% removal; no wiping |
| 3 | soy methyl ester (Steposol SB-W) | 90 | 100% removal with wiping |
| 4 | EtLPK | 180 | 100% removal with wiping |

TABLE 18-continued

| Run | Solvent | Soak Time (min) | Observation |
|---|---|---|---|
| 5 | d-limonene | 180 | 100% removal; no wiping |
| 6 | soy methyl ester (Steposol SB-W) | 180 | 100% removal with wiping |

The LPK removed the pitch after 180 minutes with wiping.

Example 13

An asphalt sealer (Sealbest 100 asphalt sealer) was applied to 4-inch×1-inch (10.16×2.54 cm) panels by dipping them into the sealer and curing at 70° C. for two hours. The coated panels were then dipped into a solution of 90 wt % EtLPK and 10 wt % Tomadol 25-9 surfactant solution under constant agitation using a stir bar that rotated at 280 rpm. The coated panels soaked in the agitated solution for 1, 2, 4, and 8 hours. At each interval, 1 panel from each solution was pulled out and wiped with a cloth to see how much of the adhesive was removed. Results are shown in Table 19.

TABLE 19

| Expt | Solvent | Wash Cycle (hr) | Observation |
|---|---|---|---|
| 1 | EtLPK | 1 | 10% removal |
| 2 | EtLPK | 2 | 30% removal |
| 3 | EtLPK | 4 | 60% removal |
| 4 | EtLPK | 8 | 95% removal |

The EtLPK-Tomadol 25-9 solution removed nearly all the asphalt after 8 hours.

Example 14

EtLPK and EtLGK were evaluated for their ability to remove labels from a child's plastic toy. The label was first removed by peeling off as much of the label that would come off. Then the area with the residual adhesive and paper from the label was soaked with the ketal for 1 minute; the area was then wiped with a towel to evaluate the performance.

Visual observation showed that when EtLPK was used as a solvent, the label residue was easily and completely removed. Some yellow color came off on the rag but there was no damage to the plastic toy.

In contrast, visual observation showed that when EtLGK was used as a removal composition, the paper was removed, but not the adhesive residue.

Example 15

The following Tables show prospective examples of formulations for a variety of uses as indicated. The amounts are in weight percent (wt %) based on the total weight of the formulations

| Component | Amount (wt %) |
|---|---|
| General Purpose Stripper Formulation | |
| EtLPK | 35 |
| Dimethyl sulfoxide (DMSO) | 29 |
| Dipropylene glycol methyl ether | 25 |
| Ethyl-3-ethoxypropionate (EEP) | 5 |
| Thickener | 1 |
| Surfactant | 5 |
| EtLPK | 16 |

| Component | Amount (wt %) |
| --- | --- |
| Propylene carbonate (PC) | 15 |
| NMP | 31 |
| Bentonite | 38 |
| Graffiti Removal Formulation | |
| DMSO | 35 |
| Solvesso ™ 150 ND* | 25-30 |
| EtLPK | 25 |
| EEP | 8 |
| Surfactant | 4 |
| Thickener | 1-5 |
| DMSO | 42 |
| EtLPK | 28 |
| d-limonene | 23 |
| Thickener | 1-5 |
| Surfactant | 4 |
| EtLPK | 40 |
| Aromatic naphtha solvent | 40 |
| NMP | 15 |
| Potassium oleate | 4 |
| Thickener | 0.05-2 |
| EtLPK | 40 |
| NMP | 30 |
| Cycloparaffinic solvent | 15 |
| Tripropylene glycol methyl ether (TPM) | 10 |
| Potassium oleate | 4 |
| Thickener | 1 |
| EtLPK | 62-65 |
| Ethyl lactate | 25 |
| BIO-SOFT N25-9† | 5 |
| Viscos ABIT NATURAL†† | 5 |
| Fragrance | 3 |
| BHT | 0.05 |
| Paint Stripper Formulation | |
| NMP | 40 |
| EtLPK | 40 |
| Propylene glycol methyl ether acetate | 17 |
| Triton ™ X-100** | 0-2 |
| Klucel-H*** | 1 |
| NMP | 36 |
| EtLPK | 30 |
| Methyl Soyate and/or terpene blend | 26 |
| Triton X-100** | 2 |
| Bentonite or fumed silica thickener | 6 |
| Hand Cleaner Gel Formulation | |
| EtLPK | 75 wt % |
| BIO-SOFT N1-7† | 15 |
| Viscos ABIT NATURAL†† | 10 |
| Fragrance | q.s. |
| Tar/Asphalt Remover Aerosol Formulation | |
| Aromatic 100 | 29 |
| EtLPK | 50 |
| COLA ® COR 600 surfactant‡ | 1 |
| Isobutane propellant | 20 |
| Parts Washer Formulation | |
| Methyl soyate | 50 |
| EtLPK | 35 |
| d-limonene | 5 |
| BIO-SOFT N1-7† | 10 |
| Engine Degreaser Formulation | |
| Soy methyl ester | 50.00 |
| EtLPK | 15.00 |
| Ethoxylated nonyl phenol surfactant | 5.00 |
| Defoamer | 3.00 |
| Mineral oil | 27.00 |
| Floor Mastic Remover Formulation | |
| EtLPK | 75 |
| BIO-SOFT N25-9† | 25 |
| Concrete Oil Stain Remover Formulation | |
| EtLPK | 75 |
| BIO-SOFT N25-9† | 25 |

*ExxonMobil Corporation
**The Dow Chemical Company
***Ashland, Inc.
†Stepan Company
††React-NTI, LLC
‡Colonial Chemical, Inc.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The endpoints of all ranges directed to the same component or property are inclusive of the endpoint and independently combinable.

Unless otherwise defined, all terms (including technical and scientific terms) used herein have the same meaning as commonly understood by one of ordinary skill in the art to which this invention belongs. The term "paint" includes any protective exterior coatings that are also known as, for example, lacquer, electropaint, shellac, top coat, base coat, color coat, and the like. The term "remover" includes compositions that clean, spot clean, and strip, and "removal" includes cleaning, spot cleaning, and stripping.

The compounds made by the above-described methods have, in embodiments, one or more isomers. Where an isomer can exist, it should be understood that the invention embodies methods that form any isomer thereof, including any stereoisomer, any conformational isomer, and any cis, trans isomer; isolated isomers thereof; and mixtures thereof.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. Alkyl groups may be straight-chained or branched. Throughout the specification, reference is made to various bivalent groups. Such groups are the same as the monovalent groups that are similarly named, and are typically indicated with an "ene" suffix. For example, a C1 to C6 alkylene group is a bivalent linking group having the same structure as a C1 to C6 alkyl group.

All cited patents, patent applications, and other references are incorporated herein by reference in their entirety.

The various embodiments described above are provided by way of illustration only and should not be construed to limit the claims attached hereto. The present invention can suitably comprise, consist of, or consist essentially of, any of the disclosed or recited elements. Thus, the invention illustratively disclosed herein can be suitably practiced in the absence of any element that is not specifically disclosed herein. Various modifications and changes will be recognized that can be made without following the example embodi-

What is claimed is:

1. A removal composition comprising a plurality of abrasive particles, an organic amine, antioxidant, biocide, colorant, corrosion inhibitor, cosolvent, defoamer, dye, enzyme, light stabilizer, odor masking agent, plasticizer, preservative, rust inhibitor, surfactant, thickener, or a combination comprising at least one of the foregoing;

from 0 to 1% water, based on the total weight of the removal composition; and an adduct of formula (1)

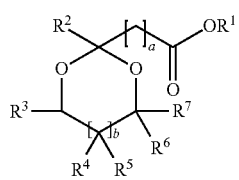

(1)

wherein $R^1$ is C1-6 alkyl, $R^2$ is hydrogen or C1-3 alkyl, each $R^3$, $R^4$, and $R^5$ is independently hydrogen or C1-6 alkyl, $R^6$ and $R^7$ are each independently hydrogen or C1-6 alkyl, a=0-3, and b=0-1.

2. The removal composition of claim 1, wherein $R^1$ is C1-6 alkyl, $R^2$ is methyl, each $R^3$, $R^4$, and $R^5$ are each independently hydrogen or C1-3 alkyl, $R^6$ is hydrogen or C1-6 alkyl, $R^7$ is hydrogen, a=1-3, and b=0-1.

3. The removal composition of claim 1, wherein $R^1$ is C1-4 alkyl, $R^2$ is methyl, $R^3$ is hydrogen, $R^6$ is hydrogen or C1-3 alkyl, $R^7$ is hydrogen, a=1-2, and b=0.

4. The removal composition of claim 1, wherein $R^1$ is C1-4 alkyl, $R^2$ is methyl, $R^3$ is hydrogen, $R^6$ is hydrogen, methyl, or ethyl, $R^7$ is hydrogen, a=2, and b=0.

5. The removal composition of claim 1, wherein the adduct is of formula (1a)

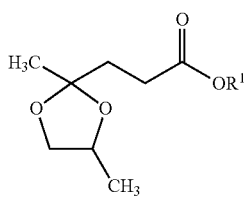

(1a)

wherein $R^1$ is a C1-4 alkyl.

6. The removal composition of claim 1, comprising a cosolvent.

7. The removal composition of claim 6, wherein the cosolvent is an amide.

8. The removal composition of claim 6, wherein the cosolvent is a sulfoxide.

9. The removal composition of claim 1, comprising an amide or sulfoxide cosolvent and an amine.

10. The removal composition of claim 1, comprising a thickener.

11. The removal composition of claim 1, comprising 1-methyl-2-pyrrolidone, a thickener, and a surfactant.

12. The removal composition of claim 1, comprising dimethyl sulfoxide, a thickener, and a surfactant.

13. The removal compositions of claim 1, wherein the removal composition is a paint remover, graffiti remover, ink remover, sealant remover, adhesive remover, mastic remover, photoresist remover, wax remover, asphalt remover, concrete cleaner, form cleaner, mold cleaner, hand cleaner, body cleaner, sap remover, oil remover, grease remover, or a combination thereof.

14. The removal compositions of claim 1, wherein the removal composition is formulated as liquid, concentrate, wipe, or aerosol.

15. A method of preparing the removal composition of claim 1, comprising:

combining a plurality of abrasive particles, an organic amine, antioxidant, biocide, builder, chelating agent, colorant, corrosion inhibitor, cosolvent, defoamer, dye, enzyme, humectant, hydrotrope, inorganic base, light stabilizer, odor masking agent, pH adjuster, pH buffering agent, plasticizer, preservative, rust inhibitor, surfactant, thickener, or a combination comprising at least one of the foregoing and the adduct of formula (1).

16. A method of removing a material on a surface of a substrate, comprising:

contacting the material on the surface of the substrate under removal conditions with a removal composition comprising 0 to 1% water, based on the total weight of the removal composition; and the adduct of formula (1)

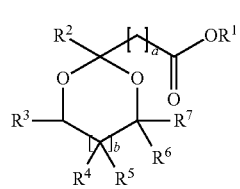

(1)

wherein $R^1$ is C1-6 alkyl, $R^2$ is hydrogen or C1-3 alkyl, each $R^3$, $R^4$, and $R^5$ is independently hydrogen or C1-6 alkyl, $R^6$ and $R^7$ are each independently hydrogen or C1-6 alkyl, a=0-3, and b=0-1; and at least partially separating the material from the substrate.

17. The method of claim 16, wherein $R^1$ is C1-6 alkyl, $R^2$ is methyl, each $R^3$, $R^4$, and $R^5$ are each independently hydrogen or C1-3 alkyl, $R^6$ is hydrogen or C1-6 alkyl, $R^7$ is hydrogen, a=1-3, and b=0-1.

18. The method of claim 16, wherein $R^1$ is C1-4 alkyl, $R^2$ is methyl, $R^3$ is hydrogen, $R^6$ is hydrogen or C1-3 alkyl, $R^7$ is hydrogen, a=1-2, and b=0.

19. The method of claim 16, wherein $R^1$ is C1-4 alkyl, $R^2$ is methyl, $R^3$ is hydrogen, $R^6$ is hydrogen, methyl, or ethyl, $R^7$ is hydrogen, a=2, and b=0.

20. The method of claim 16, wherein the adduct is of formula (1a)

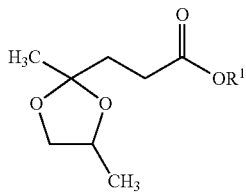

(1a)

wherein $R^1$ is a C1-4 alkyl.

21. The method of claim 16, wherein the removal composition is formulated with a plurality of abrasive particles, an organic amine, antioxidant, biocide, builder, colorant, corrosion inhibitor, cosolvent, defoamer, dye, enzyme, light stabilizer, odor masking agent, plasticizer, preservative, rust inhibitor, surfactant, thickener, or a combination comprising at least one of the foregoing.

22. The method claim 21, wherein the formulation comprises a cosolvent.

23. The method of claim 22, wherein the cosolvent is an amide.

24. The method of claim 22, wherein the cosolvent is a sulfoxide.

25. The method of claim 22, wherein the formulation comprises an amide or sulfoxide cosolvent and an amine.

26. The method of claim 22 wherein the formulation comprises a thickener.

27. The method of claim 21, comprising 1-methyl-2-pyrrolidone, a thickener, and a surfactant.

28. The method of claim 21, comprising dimethyl sulfoxide, a thickener, and a surfactant.

29. The method of claim 16, wherein the method comprises removing paint, graffiti, ink, sealant, adhesive, mastic, photoresist, mold residue, form residue, wax, asphalt, sap, oil, grease, or a combination comprising at least one of the foregoing.

* * * * *